(12) United States Patent  
Yamaguchi

(10) Patent No.: US 10,173,696 B2  
(45) Date of Patent: Jan. 8, 2019

(54) STIMULUS IMPARTING DEVICE

(71) Applicant: AISIN SEIKI KABUSHIKI KAISHA, Kariya-shi (JP)

(72) Inventor: Hideaki Yamaguchi, Okazaki (JP)

(73) Assignee: AISIN SEIKI KABUSHIKI KAISHA, Kariya-shi (JP)

( * ) Notice: Subject to any disclaimer, the term of this patent is extended or adjusted under 35 U.S.C. 154(b) by 0 days.

(21) Appl. No.: 15/552,369

(22) PCT Filed: Dec. 24, 2015

(86) PCT No.: PCT/JP2015/086145  
§ 371 (c)(1),  
(2) Date: Aug. 21, 2017

(87) PCT Pub. No.: WO2016/132653  
PCT Pub. Date: Aug. 25, 2016

(65) Prior Publication Data  
US 2018/0037236 A1    Feb. 8, 2018

(30) Foreign Application Priority Data  
Feb. 20, 2015 (JP) .................... 2015-032046

(51) Int. Cl.  
*G08B 23/00* (2006.01)  
*B60W 50/16* (2012.01)  
(Continued)

(52) U.S. Cl.  
CPC ............. *B60W 50/16* (2013.01); *A47C 7/62* (2013.01); *A61B 5/18* (2013.01); *A61M 21/00* (2013.01);  
(Continued)

(58) Field of Classification Search  
CPC ................. B60W 50/16; B60W 28/06  
(Continued)

(56) References Cited

U.S. PATENT DOCUMENTS 3,037,499 A * 6/1962 Cummins ............. B60K 28/06  
180/271  
6,676,615 B2 * 1/2004 Flick ................. A61H 23/0263  
601/57  
(Continued)

FOREIGN PATENT DOCUMENTS

DE  10 2006 018 184 A1  10/2007  
JP  2001-199296 A  7/2001  
(Continued)

OTHER PUBLICATIONS

Extended European Search Report dated Jan. 26, 2018 in Patent Application No. 15882754.3, 7 pages.  
(Continued)

*Primary Examiner* — Tai T Nguyen  
(74) *Attorney, Agent, or Firm* — Oblon, McClelland, Maier & Neustadt, L.L.P.

(57) ABSTRACT

A stimulus imparting device is provided with at least one of a first vibration device and a second vibration device, the first vibration device being provided to a vehicle seat (chair) where a driver (user) sits on and imparting a stimulus to a tendon part of the latissimus dorsi muscle of the driver, the second vibration device being provided to the vehicle seat and imparting a stimulus to a tendon part of the gluteus medius of the driver and a control device provided with a drive control unit for imparting a stimulus to the driver by performing drive control for at least one of the first vibration device and the second vibration device.

6 Claims, 15 Drawing Sheets

(51) Int. Cl.
  *B60N 2/90*   (2018.01)
  *A47C 7/62*   (2006.01)
  *A61B 5/18*   (2006.01)
  *A61M 21/00*  (2006.01)
  *G01C 21/36*  (2006.01)
  *G08B 21/06*  (2006.01)
  *G08G 1/16*   (2006.01)
  *B60H 1/00*   (2006.01)
  *B60K 28/06*  (2006.01)
  *B60N 2/02*   (2006.01)
  *B60R 21/015* (2006.01)
  *B60W 40/08*  (2012.01)

(52) U.S. Cl.
  CPC ......... *B60H 1/00742* (2013.01); *B60K 28/06* (2013.01); *B60N 2/0276* (2013.01); *B60N 2/90* (2018.02); *B60R 21/015* (2013.01); *B60W 40/08* (2013.01); *G01C 21/36* (2013.01); *G08B 21/06* (2013.01); *G08G 1/16* (2013.01); *A61M 2021/0083* (2013.01); *B60N 2002/981* (2018.02); *B60W 2040/0827* (2013.01)

(58) Field of Classification Search
  USPC ........................................ 340/575, 576, 438
  See application file for complete search history.

(56) References Cited

U.S. PATENT DOCUMENTS

| | | | |
|---|---|---|---|
| 7,311,681 B1 * | 12/2007 | Vaccarella | ...................... 601/46 |
| 8,041,484 B2 * | 10/2011 | Imai | ...................... B60W 50/16 |
| | | | 701/46 |
| 2004/0201481 A1 | 10/2004 | Yoshinori et al. | |
| 2009/0099490 A1 | 4/2009 | Durt et al. | |

FOREIGN PATENT DOCUMENTS

| | | |
|---|---|---|
| JP | 2004-284449 A | 10/2004 |
| JP | 2007-233966 A | 9/2007 |
| JP | 2008-77631 A | 4/2008 |
| JP | 2008-260444 A | 10/2008 |
| JP | 2010-172541 A | 8/2010 |
| JP | 4826441 02 | 11/2011 |
| JP | 2012-68841 A | 4/2012 |
| JP | 5538777 B2 | 7/2014 |
| WO | 2007/105694 A1 | 9/2007 |

OTHER PUBLICATIONS

International Search Report dated Apr. 5, 2016 in PCT/JP2015/086145, filed Dec. 24, 2015.

* cited by examiner

STIMULUS IMPARTING DEVICE

TECHNICAL FIELD

This invention relates to a stimulus imparting device.

BACKGROUND ART

One form of a stimulus imparting device disclosed in Patent Literature 1 has been known. As indicated in FIG. 2 of the Patent literature 1, the stimulus imparting device includes a dangerous state detecting means including a lane departing predicting/detecting means and/or a driver dozing state detecting means for vehicle and a motor control means for warning which generates a warning vibration at an electric seat by rotating a motor which operates the electric seat in positive and reverse directions by outputting a positive or reverse rotation instruction signal upon receipt of a detecting signal from the dangerous state detecting means. According to this structure, a warning by vibration to the driver can be made by utilizing a motor which is provided in advance for operating each portion of the electric seat.

Further, another form of the stimulus imparting device disclosed in Patent literature 2 has been known. As indicated in FIG. 1 of the Patent Literature 2, the stimulus imparting device is configured so that the airbag 3 expands and imparts the pressure sensitive awakening stimulus to the spinal erectors of the driver D, when the driver D, who is the subject driver of the device, becomes drowsy. The stimulus imparting device is configured so that a physiological measurement device 8 measures a muscle potential, as a parameter indicating a state of activity of the spinal erectors. The stimulus imparting device is configured so that an awakening maintaining ECU (Electronic Control Unit) 11 controls the strength of a pressure sensitive awakening stimulus imparted to spinal erectors to an appropriate strength which can activate brain cells of a driver D, based on a measured muscle potential. In addition, the stimulus imparting device is structured so that the vibration body 7 imparts the vibration stimulus to the spinal erectors. As a result, the drowsy driver D can be effectively returned to an awakening state.

CITATION LIST

Patent Literature

[Patent Literature 1] JP2008-260444 A
[Patent Literature 2] JP 2010-172541 A

SUMMARY OF INVENTION

Technical Problem(s)

According to the stimulus imparting device disclosed in the Patent Literature 1, since the vibration is imparted to the electric seat, this vibration becomes a warning to the driver to inform the driver of a dangerous state. However, even the warning can be given to the driver, the drowsiness of the driver cannot sufficiently be eliminated.

Further, according to the stimulus imparting device disclosed in the Patent Literature 2, a stimulus is given to the driver by imparting the awakening stimulus which is a pressure sensitive stimulus to the spinal erectors of the driver D by expanding the airbag 3. However, the portions to impart the stimulus according to this stimulus imparting device may not be appropriate and the drowsiness of the driver cannot be sufficiently eliminated.

Accordingly, this invention was made in consideration with the above-mentioned situation and the objective of the invention is to provide a stimulus imparting device which stimulates the portions where a high awakening effect can be expected.

Solution to Problem(s)

In order to solve the above problems, the stimulus imparting device according to the invention of claim 1, is characterized in that the stimulus imparting device includes at least one of a first vibration device provided at a chair to be positioned to face to a tendon portion of musculus latissimus dorsi of a user when the user is seated on the chair for imparting a stimulus to tendon portion of musculus latissimus dorsi of the user and a second vibration device provided at the chair to be positioned to face to a tendon portion of musculus gluteus medius of the user when the user is seated on the chair for imparting the stimulus to the tendon portion of musculus gluteus medius of the user and a control device including a drive control portion which imparts the stimulus to the user by driving at least one of the first vibration device and the second vibration device.

Effect of Invention

Accordingly, the drive control portion imparts a stimulus to at least one of the tendon portion of musculus latissimus dorsi of the user by the first vibration device and the tendon portion of musculus gluteus medius of the user by the second vibration device. In other words, the stimulus imparting device can appropriately stimulate the portions which are highly effective in awakening the user.

BRIEF EXPLANATION OF ATTACHED DRAWINGS

EMBODIMENTS FOR IMPLEMENTING INVENTION

First Embodiment

Figure 1:
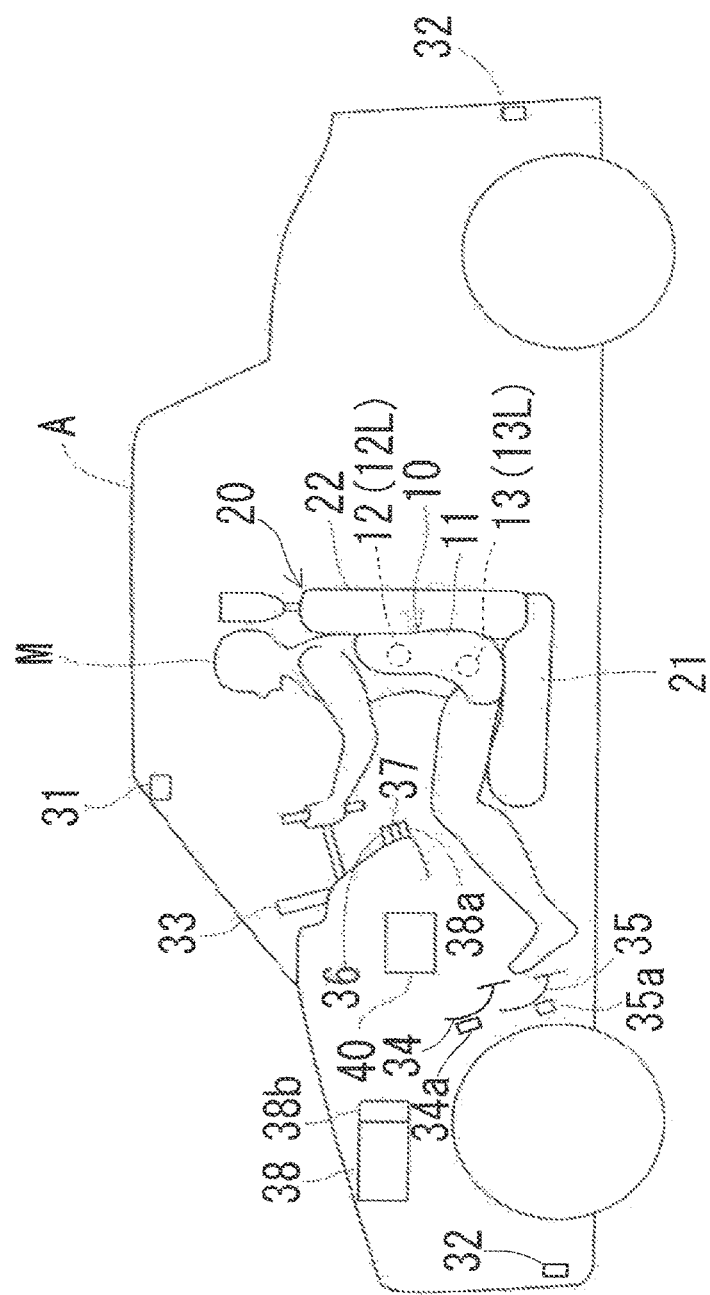
FIG. 1 is an outline of the stimulus imparting device according to a first embodiment of the invention.

The first embodiment of the stimulus imparting device of the invention will be explained hereinafter. As indicated in FIG. 1, the stimulus imparting device 10 is installed on the vehicle A. The stimulus imparting device 10 is provided at the vehicle seat 20 which is a driver's seat of the vehicle A. The vehicle seat 20 is a chair on which the driver M sits on as a user. The vehicle seat 20 is formed by a seat cushion 21 and a seat back 22.

Figure 2:
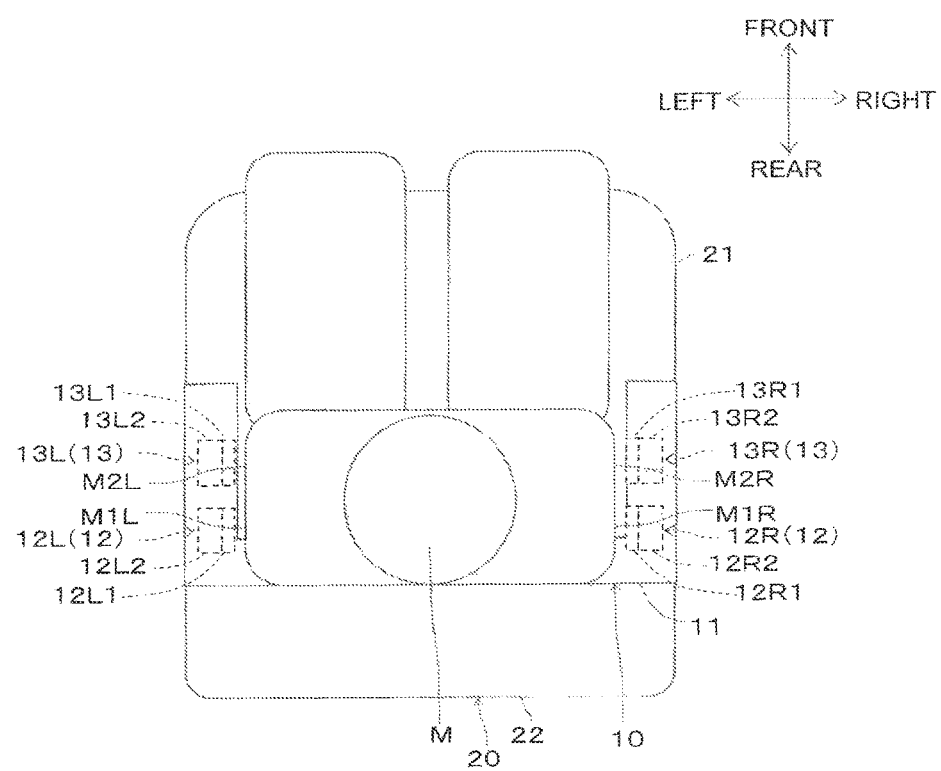
FIG. 2 is an upper plane view of the stimulus imparting device shown in FIG. 1, indicating the state that the vibration portion of the stimulus imparting device is accommodated.

The stimulus imparting device 10 includes a main body 11, a first vibration device 12 provided at the main body 11, a second vibration device 13 provided at the main body 11 and a control device 40 which controls the first vibration device 12 and the second vibration device 13, as shown in FIGS. 1 and 2. It is noted that the control device 40 may be installed on a vehicle body side (for example, at the vehicle seat 20 or a vehicle body frame, etc.), as shown in FIG. 1. Or the control device 40 may be housed in the main body 11.

The main body 11 is formed separately from the vehicle seat 20 and is detachable to or from the vehicle seat 20. The main body 11 is formed in a bucket seat shape on which the driver M can be seated. The bucket seat shape includes extremely high edges at right and left sides and is formed such that the shoulders and the bottom of the user are deeply enclosed therein, compared to the shape of a normal vehicle seat. The main body 11 is structured to cover the right and left sides, waist and thighs of body of the driver M (user).

The first vibration device 12 is a vibration device which is provided at the main body 11 for stimulating the tendon portion of musculus latissimus dorsi of the driver M. The first vibration device 12 is provided at the vehicle seat 20 through the main body 11. The first vibration device 12 is formed by a right side first vibration device (right side musculus latissimus dorsi vibration device) 12R which imparts the stimulus to the right side musculus latissimus dorsi and a left side first vibration device (left side musculus latissimus dorsi vibration device) 12L which imparts the stimulus to the left side musculus latissimus dorsi. It is preferable to arrange the right side first vibration device 12R at the portion of the main body 11 where the tendon portion M1R of the right side musculus latissimus dorsi of the driver M faces when the driver M is seated on the main body 11. It is also preferable to arrange the left side first vibration device 12L at the portion of the main body 11 where the tendon portion M1L of the left side musculus latissimus dorsi of the driver M faces when the driver M is seated on the main body 11.

The second vibration device 13 is a vibration device which is provided at the main body 11 for stimulating the tendon portion of musculus gluteus medius of the driver M. The second vibration device 13 is provided at the vehicle seat 20 through the main body 11. The second vibration device 13 is formed by a right side second vibration device (right side musculus gluteus medius vibration device) 13R which imparts the stimulus to the right side musculus gluteus medius and a left side second vibration device (left side musculus gluteus medius vibration device) 13L which imparts the stimulus to the left side musculus gluteus medius. It is preferable to arrange the right side second vibration device 13R at the portion of the main body 11 where the tendon portion M2R of the right side musculus gluteus medius of the driver M faces when the driver M is seated on the main body 11. It is also preferable to arrange the left side second vibration device 13L at the portion of the main body 11 where the tendon portion M2L of the left side musculus gluteus medius of the driver M faces when the driver M is seated on the main body 11.

Figure 3:
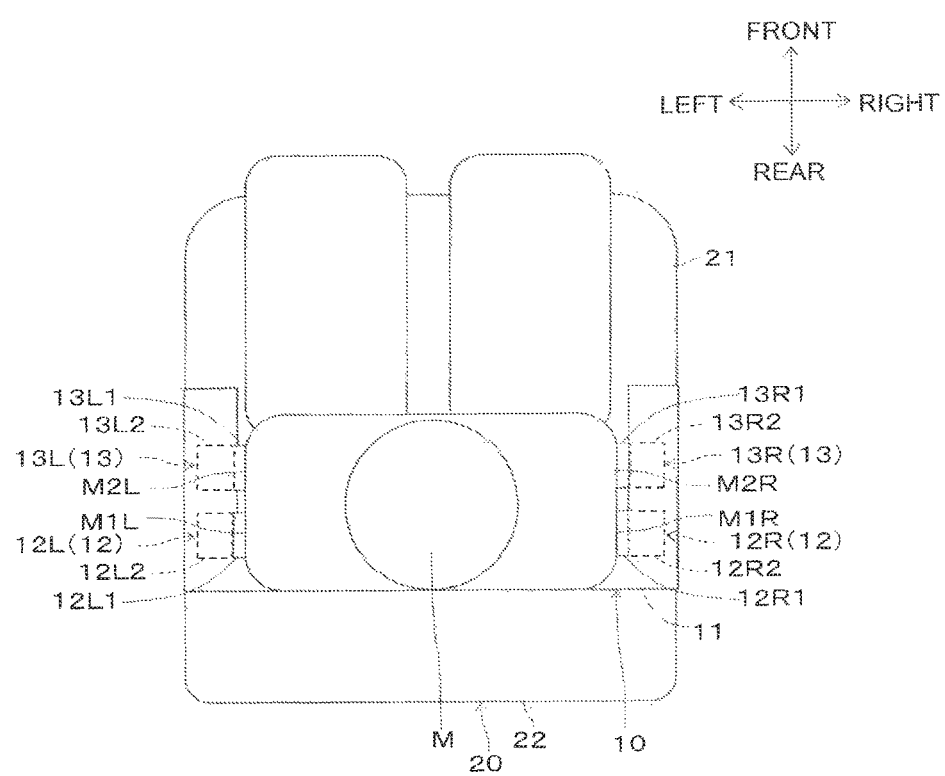
FIG. 3 is an upper plane view of the stimulus imparting device shown in FIG. 1, indicating the state that the vibration portion of the stimulus imparting device is in contact with a user.

As shown in FIGS. 2 and 3, the right side first vibration device 12R includes a vibration portion 12R1 which imparts the stimulus to the tendon portion M1R of the right side musculus latissimus dorsi by contacting therewith and a moving portion 12R2 which retreats or advances the vibration portion 12R1 relative to the driver M. The base portion of the moving portion 12R2 is fixed to the main body 11 and the tip end of the moving portion 12R2 is fixed to the vibration portion 12R1. The vibration portion 12R1 houses a motor (not shown) and is structured to generate a vibration by converting the rotation movement of the output shaft of the motor into the linear movement. It is noted that the vibration portion 12R1 may be structured to house a linear motor to generate the vibration by the linear movement of the output shaft of the motor. The moving portion 12R2 may be structured by an airbag which contracts and expands in response to the supply of the air from the air pump or discharge of the air. Further, the moving portion may be formed by a combination of the linkage mechanism and the motor.

Similarly, the left side first vibration device 12L includes a vibration portion 12L1 which imparts the stimulus to the tendon portion M1L of the left side musculus latissimus dorsi by contacting therewith and a moving portion 12L2 which retreats or advances the vibration portion 12L1. Similar to the right side first vibration device 12R, the right side second vibration device 13R includes a vibration portion 13R1 which imparts the stimulus to the tendon portion M2R of the right side musculus gluteus medius by contacting therewith and a moving portion 13R2 which retreats or advances the vibration portion 13R1. The left side second vibration device 13L, similar to the right side first vibration device 12R, includes a vibration portion 13L1 which imparts the stimulus to the tendon portion M2L of the left side musculus gluteus medius by contacting therewith and a moving portion 13L2 which retracts or advances the vibration portion 13L1. It is noted that the stimulus imparting device 10 may be structured to be housed in the vehicle seat 20.

Figure 4:
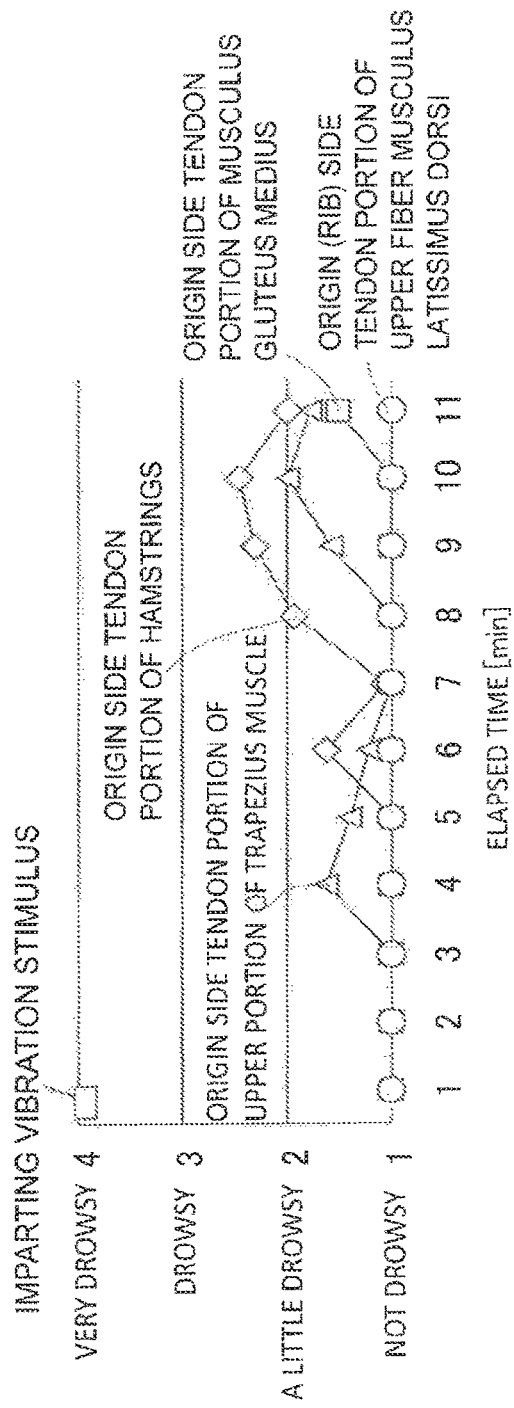
FIG. 4 is a view showing the drowsiness generation suppression effect at each stimulus imparting portion (at each skeletal muscle type)

The reason why the portions (i.e., the tendon portion of the musculus latissimus dorsi and the tendon portion of the musculus gluteus medius) are set as the specified portions to which the stimulus is imparted, will be explained hereinafter. The inventor of this application found out by experimental work that a highly effective awakening effect is expected at the tendon portion of particular skeletal muscle (including muscle tendon transfer portion). The particular skeletal muscle corresponds to the musculus latissimus dorsi and the musculus gluteus medius. FIG. 4 shows the experimental work result of the case in which a vibration stimulus is imparted to the tendon portions of a plurality of skeletal muscles when the subject of the experiment is in a first sleep level in which the subject of the experiment does not feel sleepy or drowsy, wherein the horizontal axis indicates the elapsed time from the time the vibration stimulus is imparted and the vertical axis indicates the degree of the sleep level.

The vibration stimulus is consecutively imparted for thirty (30) seconds with the frequency of 100 Hz wave and each vibration stimulus is imparted with the same wave state. This stimulus is imparted by changing the subject portions of skeletal muscle to measure the sleep level. The sleep level is determined by self-reporting by the subject of the experiment or may be determined by measurement. The sleep level change when the stimulus is imparted to the origin side tendon portion of musculus gluteus medius is indicated with the square mark, the sleep level change when the stimulus is imparted to the origin side tendon portion of hamstrings is indicated with the rhombus mark, the sleep level change when the stimulus is imparted to the origin (rib bone) side tendon portion of upper fiber musculus latissimus dorsi is indicated with the circle mark and the sleep level change when the stimulus is imparted to the origin side tendon portion of upper fiber trapezius muscle is indicated with the triangle mark. It is noted that hamstrings is a general term for the muscle at the posterior surface of lower limb muscles and includes biceps femoris muscle, semimembranosus muscle and semitendinosus muscle, etc.

Apparent from the experiment result, the sleep levels upon imparting the stimulus to the hamstrings and trapezius muscle change largely to the sleepy side from the early timing. To this, the sleep levels upon imparting the stimulus to the musculus latissimus dorsi and musculus gluteus medius keep the first sleep level in which the subject does not feel drowsy for relatively longer time period. Accordingly, imparting stimulus to the tendon portions of the musculus latissimus dorsi and musculus gluteus medius exhibits a high effect of suppressing generation of drowsiness or sleepiness. In other words, a high awakening effect can be maintained.

It is noted that a sensor called "muscle spindle" which senses the state of muscle exists in the skeletal muscle. The information that the muscle spindle is activated is transferred to the brainstem reticular formation and activation level of the brain is raised (awakening level is raised). Further, the musculus latissimus dorsi and musculus gluteus medius are the type I fiber which includes many muscle spindles. Further, since the musculus latissimus dorsi and musculus gluteus medius are arranged so that a plurality of skeletal muscles does not lie one on top of another, they do not receive any influence from the skeletal muscle of different reaction characteristics and they have an effect that they keep stable state.

Figure 5:
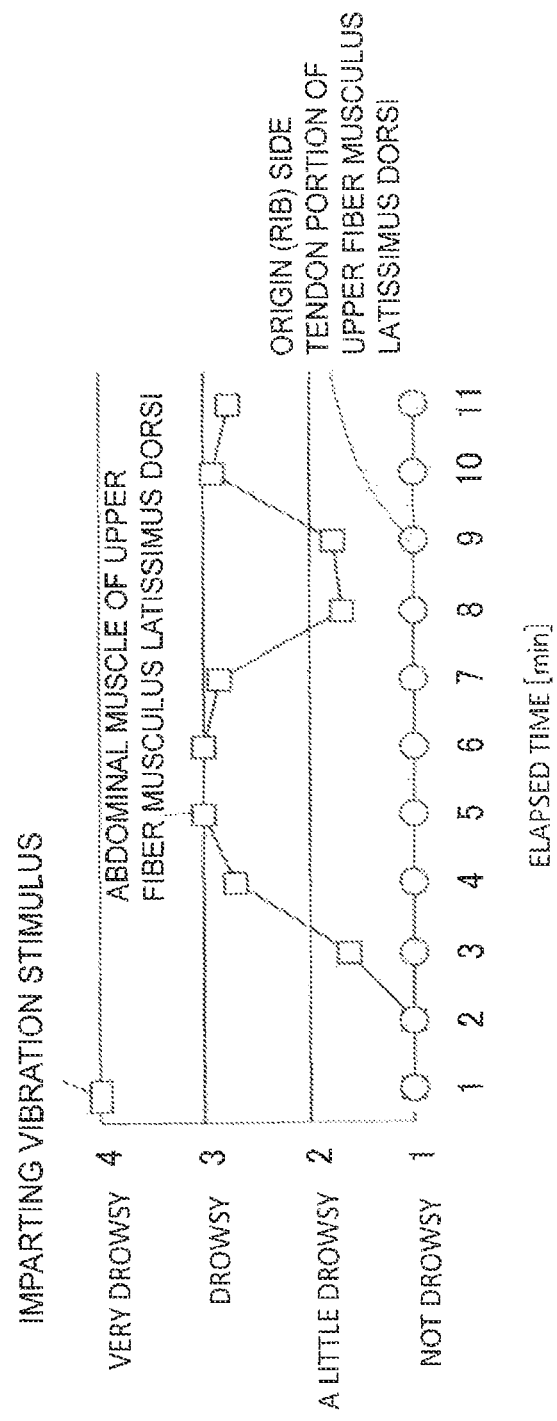
FIG. 5 is a view showing the drowsiness generation suppression effect at each stimulus imparting portion (at each abdominal muscle and tendon portion of the same skeletal muscle)

Further, the inventor of the application found out by the experimental work that the tendon portions have more advantageous effect than the abdominal muscles in the musculus latissimus dorsi and musculus gluteus medius. FIG. 5 shows the experimental result of the case that the vibration stimulus is imparted to the abdominal muscle and tendon portion of the same skeletal muscle, when the subject of the experiment is in the first sleep level in which the subject does not feel sleepy or drowsy. The horizontal axis of the drawing indicates the elapsed time from the time when the simulation is imparted and the vertical axis indicates the degree of the sleep level.

The vibration stimulus is consecutively imparted for thirty (30) seconds with the frequency of 100 Hz wave and each vibration stimulus is imparted in the same wave. This stimulus is imparted by changing the stimulus portion at the same skeletal muscle to measure the sleep level. The sleep level is determined by self-reporting by the subject of the experiment or may be determined by measurement. The sleep level change when the stimulus is imparted to the abdominal muscles of upper fiber musculus latissimus dorsi is indicated with the square mark and the sleep level change when the stimulus is imparted to the origin (rib bone) side tendon portion of upper fiber musculus latissimus dorsi is indicated with circle mark.

Apparent from the experiment result, the sleep level upon imparting the stimulus to the abdominal muscles changes largely to the drowsy side from the early timing. To this, the sleep level upon imparting the stimulus to the origin (rib bone) side tendon portion keeps the first sleep level in which the subject does not feel drowsy for relatively longer time period. Accordingly, stimulus to the tendon portions exerts a high effect for suppressing generation of drowsiness or sleepiness. In other words, a high awakening effect can be maintained.

Figure 6:
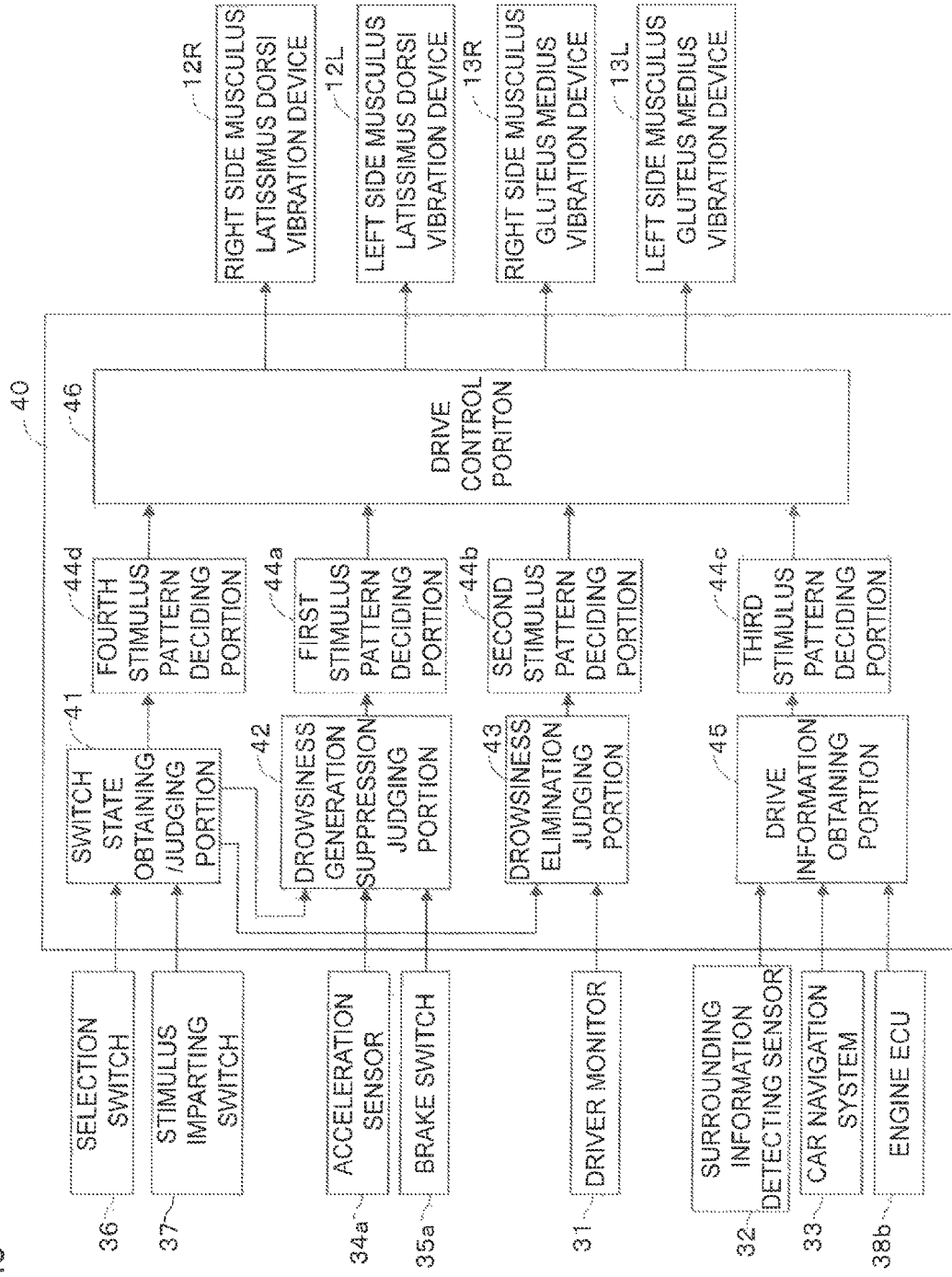
FIG. 6 is a block diagram showing a control device indicated in FIG. 1.

As shown in FIG. 6, a driver monitor 31, a surrounding information detecting sensor 32, a car-navigation system 33, an acceleration sensor 34a, a brake switch 35a, a selection switch 36 and a stimulus imparting switch 37 are electrically connected to the control device 40.

The driver monitor 31 is installed in a vehicle compartment of the vehicle A (for example, dashboard or room mirror, etc.) as shown in FIG. 1 and the monitor 31 includes for example, a camera and is used for monitoring the behavior of the driver M. The driver monitor 31 detects whether the driver M is in a drowsy state or not, from the image of the expression or the look of the driver M which is taken by the camera. For example, when the driver M frequently gives yawns, increases (or, decreases) blinking, or closes the eyes, the monitor 31 detects that the driver M is in a drowsy state. Such detected result is outputted to the control device 40. It is noted that the driver monitor 31 may be structured such that the image of driver's expression information taken by the camera is outputted to the control device 40 and the control device 40 may judge whether the driver is in a drowsy state or not, based on the outputted expression information.

The surrounding information detecting sensor 32 is installed at the vehicle A front portion (such as a front bumper or a front grill), at a front portion of the vehicle compartment (such as in the vicinity of the room mirror) or at a rear portion of the vehicle (for example, rear bumper and a rear portion of the vehicle compartment) and includes a millimeter wave radar and a camera for detecting the surrounding information of the surrounding of the vehicle A. The surrounding information of the vehicle A includes for example, the existence of obstacles (vehicle, people, etc.) in the periphery of the vehicle in front/rear direction or around the sides of the vehicle. The detected result of the surrounding information detecting sensor 32 is outputted to the control device 40.

The car-navigation system 33 is installed in the vehicle compartment (for example, dashboard) and the car-navigation system 33 is used for guiding the position of the vehicle A and the route to a target place during vehicle running. The car-navigation system 33 guides the lane changing operation and right/left turning of the vehicle A. The content of the guidance by the system is outputted to the control device 40.

The acceleration sensor 34a is installed in the vicinity of the acceleration pedal 34 for detecting the opening degree and ON/OFF operation of the acceleration pedal 34. The detected result of the acceleration sensor 34a is outputted to the control device 40. The brake switch 35a is installed in the vicinity of the brake pedal 35 for detecting ON/OFF operation of the brake pedal 35. The detected result of the brake switch 35a is outputted to the control device 40.

The selection switch 36 is used as a switch for selecting either the drowsiness generation suppression assist or the drowsiness elimination assist and the selection result is outputted to the control device 40. A selection position which indicates the state that neither of the drowsiness generation suppression assist and the drowsiness elimination assist are selected, may be provided. The drowsiness generation suppression assist is a control which imparts the stimulus to the driver M when the driver M is not drowsy (first sleep level) to suppress the generation of the drowsiness for a predetermined time from the time when the stimulus is imparted. The predetermined time is defined depending on the individual. The drowsiness elimination assist is a control which imparts the stimulus to the driver M when the driver M feels sleepy or drowsy (third sleep level) to eliminate the drowsiness. The sleep level is classified into four steps, the first sleep level, in which one does not feel sleepy or drowsy, the second sleep level, in which one feels sleepy or drowsy a little, the third sleep level, in which one feels sleepy or drowsy and the fourth sleep level, in which one feels very sleepy or drowsy.

The stimulus imparting switch 37 is a switch which imparts the stimulus to the driver M upon request by the driver M itself. The ON/OFF state of the stimulus imparting switch 37 is outputted to the control device 40. When the stimulus imparting switch 37 is turned ON, each of the vibration devices 12R, 12L, 13R and 13L is driven with a predetermined stimulus pattern of imparting the stimulus to the driver M. The stimulus imparting switch 37 is structured such that the stimulus is imparted to the driver M, every time the switch is turned ON, or may be structured such that the stimulus is imparted to the driver M, every predetermined time during the switch 37 being turned ON.

The control device 40 includes a switch state obtaining/judging portion 41, a drowsiness generation suppression judging portion 42, a drowsiness elimination judging portion 43 and each stimulus pattern deciding portion 44a through 44d, a drive information obtaining portion 45 and a drive control portion 46, as shown in FIG. 6.

When the selection switch 36 selects any one of the drowsiness generation suppression assist state, drowsiness elimination assist state and non-selected state, the switch state obtaining/judging portion 41 obtains the selection result from the selection switch 36 and judges the assist states or non-selected state selected by the selection switch 36. Further, the switch state obtaining/judging portion 41 obtains the ON/OFF state of the stimulus imparting switch 37 from the stimulus imparting switch 37 and judges whether or not the stimulus imparting switch 37 is turned ON.

The drowsiness generation suppression judging portion 42 is a first judging portion which judges whether or not the suppression of drowsiness of the driver M seated on the vehicle seat 20 is necessary (drowsiness generation suppression judgement). The drowsiness generation suppression judging portion 42 judges whether or not the suppression of drowsiness of the driver M is necessary, based on the operation of operating member by the driver M. The drowsiness generation suppression judging portion 42 executes the drowsiness generation suppression judgement, when the judgement result of the selection switch 36 that the drowsiness generation suppression assist is selected is obtained from the switch state obtaining/judging portion 41. The operating member includes, for example, an acceleration pedal 34 and the brake pedal 35.

The drowsiness generation suppression judging portion 42 obtains the detection result of the acceleration sensor 34a from the acceleration sensor 34a and at the same time obtains the detection result of the brake switch 35a from the brake switch 35a. The drowsiness generation suppression judging portion 42 judges whether or not the suppression of generation of drowsiness of the driver M is necessary, based on these detection results. For example, the drowsiness generation suppression judging portion 42 judges that the suppression of generation of drowsiness of the driver M is necessary, when the acceleration pedal 34 is consecutively depressed for a predetermined time or when the brake pedal 35 is depressed. It is noted that the generation suppression judging portion 42 may be structured such that the driver M can select either of the operations (acceleration operation and brake operation) to be the subject operation for judgement.

The drowsiness elimination judging portion 43 is a second judging portion which judges whether or not the elimination of drowsiness of the driver M seated on the vehicle seat 20 is necessary (drowsiness elimination judgement). The drowsiness elimination judging portion 43 executes the drowsiness elimination judgement, when the judgement result of the selection switch 36 that the drowsiness elimination assist is selected is obtained from the switch state obtaining/judging portion 41.

The drowsiness elimination judging portion 43 obtains the detected result of the driver monitor 31 (result of judgement whether the driver M is drowsy or not) from the driver monitor 31. The drowsiness elimination judging portion 43 judges that the elimination of the drowsiness of the driver M is necessary, when the detection result that the driver M is drowsy is obtained. It is noted that the driver monitor 31 detects that the driver M is drowsy, if the driver M changes the expression, for example, the driver M frequently gives yawns, increases (or, decreases) blinking, or closes the eyes.

It should be noted that the judgment subject expression change may be selectable by the driver M. It is also possible to memorize expression changes before and after the stimulus assigning switch 37 is turned on to derive a characteristic expression change that is easy for the driver M and change the expression change with the feature as the judgment subject expression change.

The fourth stimulus pattern deciding portion 44d decides the fourth stimulus pattern when the fourth stimulus pattern 44d obtains the detection result that the stimulus imparting switch 37 is turned ON from the switch state obtaining/judging portion 41. The fourth stimulus pattern is the basic stimulus pattern and it is preferable to set the frequency thereof to be about 90 to 110 Hz and one time consecutive imparting time to be about 20 to 40 seconds. More preferably, the frequency is set to be 100 Hz and the one time consecutive imparting time is set to be 30 seconds.

Figure 7:
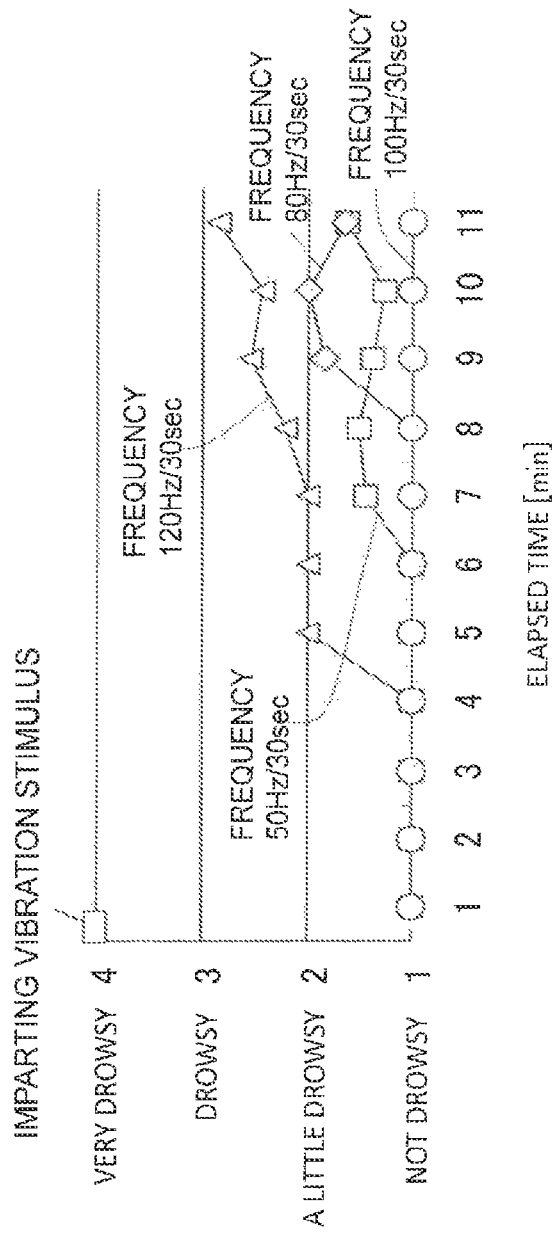
FIG. 7 is a view showing the drowsiness generation suppression effect of every frequency of vibration stimulus.

The optimum frequency can be determined by the experiment. The experiment result is shown in FIG. 7. FIG. 7 indicates the experiment result when the vibration stimulus is imparted to the upper fiber origin (rib bone) side tendon portion (including muscle tendon transfer portion) among the tendon portions of the musculus latissimus dorsi, under the state that the subject driver is in the first sleep level in which the subject does not feel drowsy. In the drawing, the horizontal axis indicates the lapsed time from the time of imparting vibration stimulus and the vertical axis indicates the degree of the sleep level.

The consecutive imparting time is fixed to 30 seconds and the frequency of the stimulus wave is changed at 50 through 120 Hz and the sleep level is measured. The sleep level is determined by self-reporting by the subject of the experiment or may be determined by measurement. The sleep level change when the stimulus with the frequency of 50 Hz is imparted for consecutively 30 seconds is indicated with the square mark, the sleep level change when the stimulus with the frequency of 80 Hz is imparted for consecutively 30 seconds is indicated with the rhombus mark, the sleep level change when the stimulus with the frequency of 100 Hz is imparted for consecutively 30 seconds is indicated with the circle mark and the sleep level change when the stimulus with the frequency of 120 Hz is imparted for consecutively 30 seconds is indicated with the triangle mark. Apparent from the experiment result above, the optimum frequency is 100 Hz. From the frequency of 100 Hz being the peak, the sleep level becomes increasing to the drowsy side, regardless of frequency increasing or decreasing therefrom.

Figure 8:
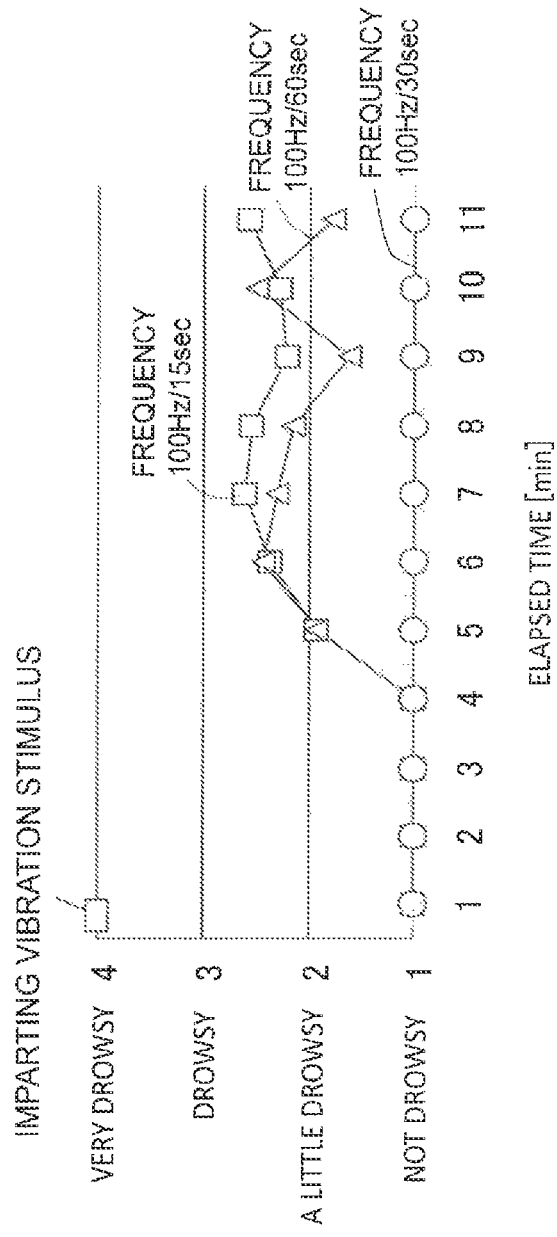
FIG. 8 is a view showing the drowsiness generation suppression effect at every imparting time of vibration stimulus.

The optimum one time consecutive imparting time can be determined by the experiment. The experiment result is shown in FIG. 8. FIG. 8 indicates the experiment result when the vibration stimulus is imparted to the upper fiber origin (rib bone) side tendon portion (including muscle tendon transfer portion) among the tendon portions of the musculus latissimus dorsi, under the state that the subject driver is in the first sleep level in which the subject does not feel drowsy. In the drawing, the horizontal axis indicates the elapsed time from the time of imparting vibration stimulus and the vertical axis indicates the degree of the sleep level.

The frequency is fixed to 100 Hz and the consecutive imparting time is changed in 15 through 60 seconds and the sleep level is measured. The sleep level is determined by self-reporting by the subject of the experiment or may be determined by measurement. The sleep level change when the stimulus with the frequency of 100 Hz is imparted for consecutively 15 seconds is indicated with the square mark, the sleep level change when the stimulus with the frequency of 100 Hz is imparted for consecutively 30 seconds is indicated with the circular mark and the sleep level change when the stimulus with the frequency of 100 Hz is imparted for consecutively 60 seconds is indicated with the triangle mark. Apparent from the experiment result above, the optimum consecutive imparting time is 30 seconds. The sleep level becomes increasing to the drowsy side from the early timing, regardless of the imparting time of 15 seconds or 60 seconds. As apparent from the experiment results above, the imparting stimulus with the frequency of 100 Hz and one time consecutive imparting time of 30 seconds exert the highest awakening effect. It is noted here the same result can be obtained by the experiment to tendon portion (particularly origin side tendon portion including muscle tendon transfer portion) of musculus gluteus medius, instead of the experiment to the tendon portion of the musculus latissimus dorsi.

The fourth stimulus pattern may be the stimulus pattern in which all of the vibration devices 12R, 12L, 13R and 13L are simultaneously operated to vibrate repeatedly (all vibrations), or may be the stimulus pattern in which only the right side first vibration device 12R and the left side first vibration device 12L are simultaneously operated to vibrate repeatedly (tendon portions of the musculus latissimus dorsi vibration) or may be the stimulus pattern in which only the right side second vibration device 13R and the left side second vibration device 13L are simultaneously operated to vibrate repeatedly (tendon portions of the musculus gluteus medius vibration). It is further noted that the stimulus pattern may be the pattern in which tendon portions of the musculus latissimus dorsi vibration and the musculus gluteus medius are all vibrated at the first time (all vibrations), then the tendon portion of the musculus latissimus dorsi is vibrated at the second time, and then the tendon portion of the musculus gluteus medius is vibrated (the musculus gluteus medius vibration), thereafter the above three vibrations are repeated. The order of the stimulus vibration is not limited to the above order. It is further noted that the stimulus pattern may include the pattern in which only the right side vibration devices 12R, 13R are simultaneously operated to vibrate (right side vibration), or only the left side vibration devices 12L, 13L are simultaneously operated to vibrate (left side vibration).

The first stimulus pattern deciding portion 44*a* decides the first stimulus pattern that suppresses the generation of drowsiness of the driver M when the suppression of generation of the drowsiness of the driver M is judged to be necessary by the judgement of the drowsiness generation suppression judging portion 42. The first stimulus pattern is basically the same with the fourth stimulus pattern. The second stimulus pattern deciding portion 44*b* decides the second stimulus pattern that eliminates the drowsiness of the driver M when the elimination of the drowsiness of the driver M is judged to be necessary by the judgement of the drowsiness elimination judging portion 43. The second stimulus pattern is basically the same with the fourth stimulus pattern.

The drive information obtaining portion 45 obtains the drive information which relates to a driving state of the vehicle A. The drive information which relates to the driving state of the vehicle A includes at least one of the information relating to a vehicle surrounding information which relates to the surroundings of the vehicle A and the information relating to the guide information which relates to a driving guide of the vehicle A. The drive information obtaining portion 45 obtains the vehicle surrounding information from the surrounding information detecting sensor 32 and at the same time obtains the guide information from the car-navigation system 33.

The third stimulus pattern deciding portion 44*c* decides the respective third stimulus pattern which is corresponding to the type of the drive information relating to the driving of the vehicle A obtained by the drive information obtaining portion 45. The drive information relating to the vehicle surrounding information will be explained hereinafter. When an obstacle is detected in a rearward of the vehicle A (Particularly, in a position close to the vehicle A), it is preferable to decide the pattern of the third stimulus pattern to the stimulus pattern in which only the right side first vibration device 12R and the left side first vibration device 12L are simultaneously vibrated repeatedly (musculus latissimus dorsi vibration). When an obstacle is detected in a frontward of the vehicle A (Particularly, in a position close to the vehicle A), it is preferable to decide the pattern of the third stimulus pattern to the stimulus pattern in which only the right side second vibration device 13R and the left side second vibration device 13L are simultaneously vibrated repeatedly (musculus gluteus medius vibration). When an obstacle is detected in a right side of the vehicle A, it is preferable to decide the pattern of the third stimulus pattern to the stimulus pattern in which only the right side first vibration device 12R and the right side second vibration device 13R are simultaneously vibrated repeatedly (right side vibration). When an obstacle is detected in a left side of the vehicle A, it is preferable to decide the pattern of the third stimulus pattern to the stimulus pattern in which only the left side first vibration device 12L and the left side second vibration device 13L are simultaneously vibrated repeatedly (left side vibration).

As explained, it is preferable to position the vibration devices (vibration imparting portions) which impart the stimulus vibration to the obstacle in a direction corresponding to the direction in which the obstacle exists. Further, when the obstacle is positioned in the right front of the vehicle A, the third stimulus pattern is decided to be the stimulus pattern repeatedly vibrated only by the right side second vibration device 13R. Further, when the obstacle is positioned in the left front of the vehicle A, the third stimulus pattern is decided to be the stimulus pattern repeatedly vibrated only by the left side second vibration device 13L. Still further, when the obstacle is positioned in the right rear of the vehicle A, the third stimulus pattern is decided to be the stimulus pattern repeatedly vibrated only by the right first vibration device 12R and when the obstacle is positioned in the left rear of the vehicle A, the third stimulus pattern is decided to be the stimulus pattern repeatedly vibrated only by the left side first vibration device 12L.

Figure 9:
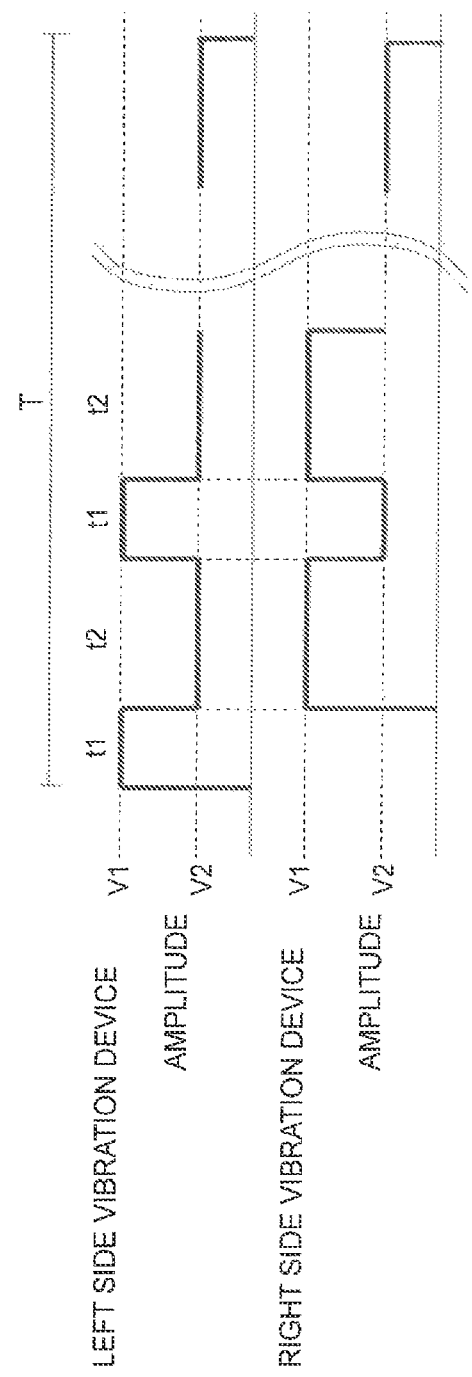
FIG. 9 is a view showing an example of the third stimulus pattern when the lane change is made.

The drive information relating to the guide information will be explained hereinafter. When the vehicle A changes the lane (lane departing), for example, when the vehicle A changes the lane to the right lane, as shown in FIG. 9, the third stimulus pattern is decided to the stimulus pattern in which only the left side vibration (by the left side vibration devices 12L and 13L) is made with the vibration amplitude V1 for the first predetermined time t1 from the start of the lane departing guide, and then the left side vibration is made with the reduced amplitude of V2 for the second predetermined time t2 and at the same time, the right side vibration (by right side vibration device 12R and 13R) is made with the amplitude of V1. Then the left side vibration is made with the amplitude V1 for the first predetermined time t1 and at the same time, the right-side vibration is made with the reduced amplitude of V2. This stimulus pattern is repeatedly made until the lane departing guide is finished. When the lane departing guide is finished, the stimulus imparting stops after imparting the same amplitude vibration at right and left sides. It is noted that when the vehicle moves to the left lane, the first vibration starts with the right-side vibration. Further, it is noted that the second predetermined time t2 is set to be longer than the first predetermined time t1. The vibration amplitude V2 is preferably set to be within from the value of a quarter of the amplitude V1 to the value of three quarters of the amplitude V1. More preferably the value V2 is set to be the half of the value V1. The total vibration imparting time T is preferably set to be 20 to 40 seconds. As explained, the guiding direction and the order of the position of the vibrating devices for imparting a stimulus (vibration imparting portion) are configured to correspond to each other.

Figure 10:
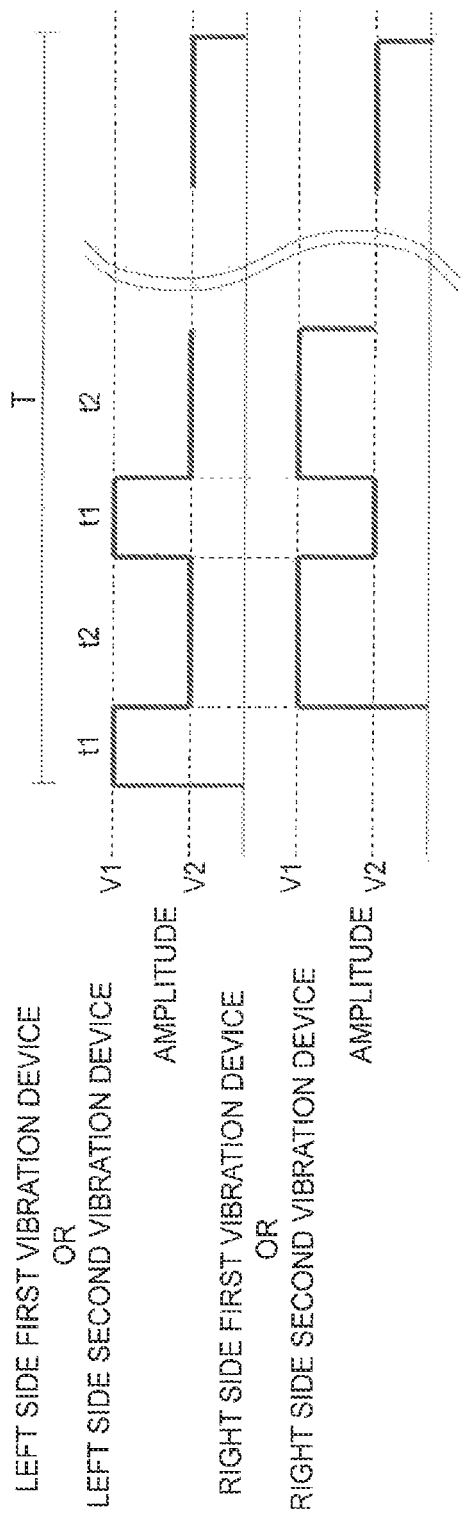
FIG. 10 is a view showing an example of the third stimulus pattern when the turning is made at the intersection.

The turning of the vehicle A at the intersection will be explained. For example, when the vehicle A turns right, as shown in FIG. 10, the third stimulus pattern is indicated as a stimulus pattern, as similar to the case of lane departing guide, in which, firstly, only the left side vibration (by the left side vibration device 12L or 13L) with the vibration amplitude V1 for the first predetermined time t1 from the start of right turn guiding is executed, then the left side vibration is executed with a reduced amplitude V2 for the second predetermined time t2 and at the same time the right side vibration (by the right side vibration device 12R or 13R) with the amplitude V1, then the left side vibration with the amplitude V1 for the first predetermined time t1 and at the same time the right side vibration with the reduced amplitude V2 are executed. This third stimulus pattern is repeated until the turning guide at the intersection is finished. When the turning guide is finished, the stimulus imparting operation stops after imparting the same amplitude vibration at the right and left sides. It is noted that when the vehicle turns left, the first vibration starts with the right-side vibration. As explained, the guiding direction and the order of the position of the vibration devices for imparting a stimulus (vibration imparting portions) are configured to correspond to each other. Further, the drive information relating to the ignition switch ON state information which includes the judgement of the state of the ignition switch 38a, whether or not the switch 38a is ON. The ignition switch ON state information is the engine activation state information which indicates whether or not the engine 38 is in activated state. In other words, when the ignition switch 38a is ON, the engine 38 is in the activated state and when the ignition switch 38a is OFF, the engine 38 is in a non-activated state. The drive information obtaining portion 45 obtains the ignition switch ON state information (i.e., the engine activated state information) from the engine ECU 38b. The engine ECU 38b monitors the ON state of the ignition switch 38a and the activated state of the engine 38. When the third stimulus pattern deciding portion 44c obtains the ignition switch ON state information (i.e., the engine activated state information) from the drive information obtaining portion 45, the third stimulus pattern deciding portion 44c decides the third stimulus pattern which corresponds to the ignition switch ON state information. In this case, the third stimulus pattern is basically the same with the fourth stimulus pattern. In more detail, the third stimulus pattern is the stimulus pattern in which the all vibrations, the musculus latissimus dorsi vibration and the musculus gluteus medius vibration, etc., are imparted when the ignition switch 38a is turned ON. Further, the third stimulus pattern is the stimulus pattern in which the all vibrations, the musculus latissimus dorsi vibration and the musculus gluteus medius vibration, etc., are imparted at the time when the ignition switch 38a is further turned ON when the ignition switch 38a has been already turned ON.

The drive control portion 46 drives at least one of the first vibration device 12 and the second vibration device 13 according to the stimulus patterns decided by the stimulus pattern deciding portions 44a through 44d, thereby to impart the stimulus to the driver M. When the suppression of generation of the drowsiness of the driver M is judged to be necessary, the drive control portion 46 drives each vibration device 12R, 12L, 13R and 13L based on the first stimulus pattern to impart the stimulus to the driver M to execute the drowsiness generation suppression assist operation. Thus, the generation of drowsiness of the driver M can be suppressed. Further, when the elimination of the drowsiness of the driver M is judged to be necessary, the drive control portion 46 drives each vibration device 12R, 12L, 13R and 13L based on the second stimulus pattern to impart the stimulus to the driver M to execute the drowsiness elimination assist operation. Further, when the driver M, itself requires the stimulus (when the driver M turns the stimulus imparting switch 37 ON), the drive control portion 46 drives each vibration device 12R, 12L, 13R and 13L based on the fourth stimulus pattern to impart the stimulus to the driver M to execute the drowsiness elimination assist operation. Further, when the drive information is informed for guiding the driver M, the drive control portion 46 drives each vibration device 12R, 12L, 13R and 13L based on the third stimulus pattern to impart the stimulus to the driver M to execute the drive information informing assist operation.

The effect of the imparting of the stimulus to the driver M will be explained. Among the various effects of the stimulus imparting to the particular body portions of the driver M, the drowsiness generation suppression can exert the effect that the stimulus imparted to the tendon portions of musculus latissimus dorsi and the musculus gluteus medius can keep the first sleep level in which drowsiness is not generated for a relatively longer period of time, as shown in FIGS. 4 and 5. Accordingly, the stimulus imparted to the tendon portions of musculus latissimus dorsi and the musculus gluteus medius has a high drowsiness suppression effect and can keep the high awakening effect.

Figure 11:
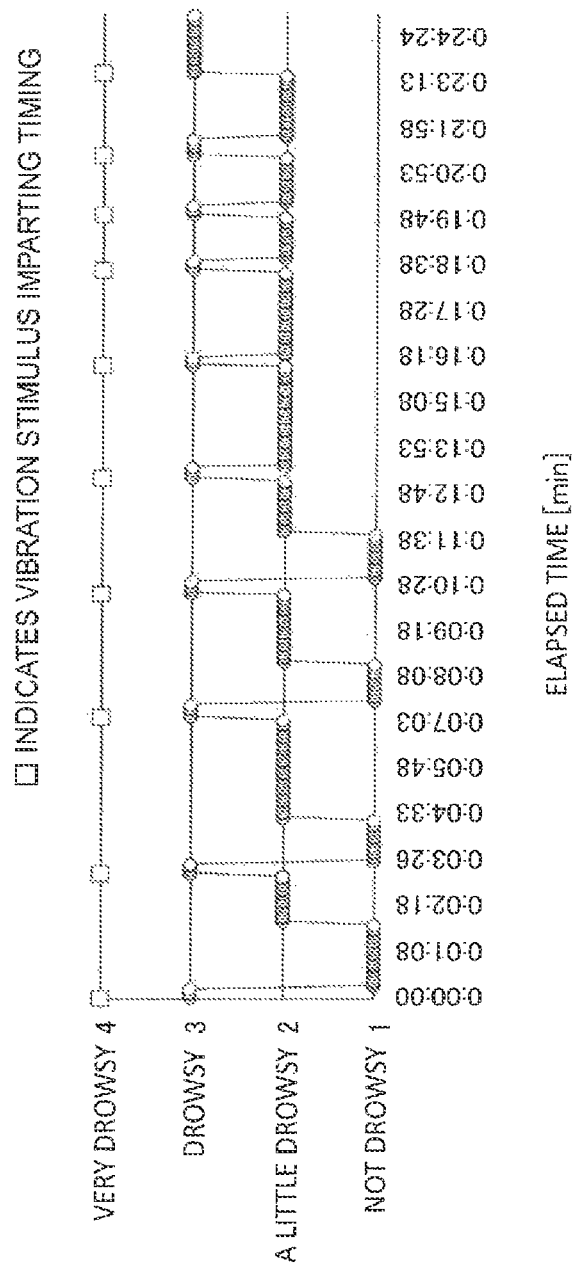
FIG. 11 is a view showing a drowsiness eliminating effect when the vibration stimulus is imparted to the tendon portion of musculus latissimus dorsi.
Figure 12:
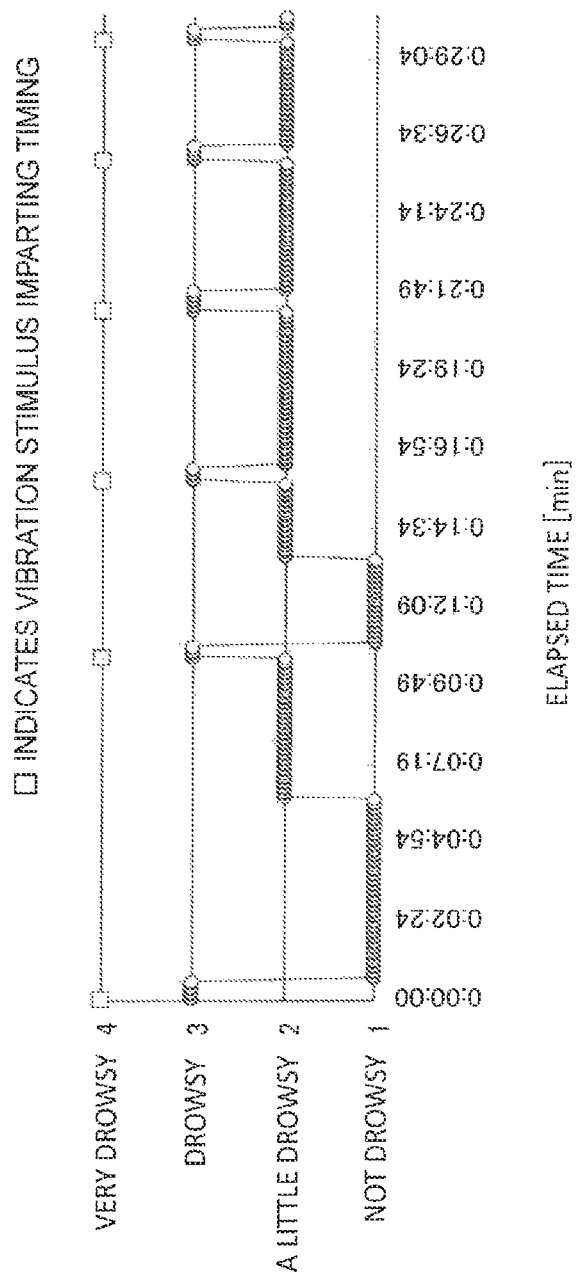
FIG. 12 is a view showing a drowsiness eliminating effect when the vibration stimulus is imparted to the tendon portion of musculus gluteus medius.

Among the various effects of the stimulus imparting to the particular body portions of the driver M, the drowsiness elimination effect is indicated in FIGS. 11 and 12. In FIG. 11, the experiment result is shown when the vibration stimulus is imparted to the tendon portion (including muscle tendon transfer portion) of musculus latissimus dorsi at the upper fiber origin side (rib) when the subject is at the third sleep level in which the subject feels drowsy. The vibration stimulus is imparted with the frequency of 100 Hz for 30 seconds consecutively. The square mark indicates the timing of imparting the vibration stimulus and this timing agrees with the timing when the subject reaches the third sleep level in which the subject feels drowsy. Immediately after the imparting of the vibration stimulus, the sleep level becomes the first sleep level in which the subject does not feel drowsy. Thus, high drowsiness elimination effect by imparting the vibration stimulus can be confirmed.

In FIG. 12, the experiment result is shown when the vibration stimulus is imparted to the tendon portion (including muscle tendon transfer portion) of musculus gluteus medius at the origin side, when the subject is at the third sleep level in which the subject feels drowsy. The vibration stimulus is imparted with the frequency of 100 Hz for 30 seconds consecutively. The square mark indicates the timing of imparting the vibration stimulus and this timing agrees with the timing when the subject reaches the third sleep level in which the subject feels drowsy. Immediately after the imparting of the vibration stimulus, the sleep level becomes the first sleep level in which the subject does not feel drowsy. Thus, high drowsiness elimination effect by imparting the vibration stimulus can be confirmed. It is noted that the drowsiness elimination effect (drowsiness generation suppression effect) when the stimulus is imparted to the musculus gluteus medius is kept longer than the drowsiness elimination effect when the stimulus is imparted to the musculus latissimus dorsi.

Figure 13:
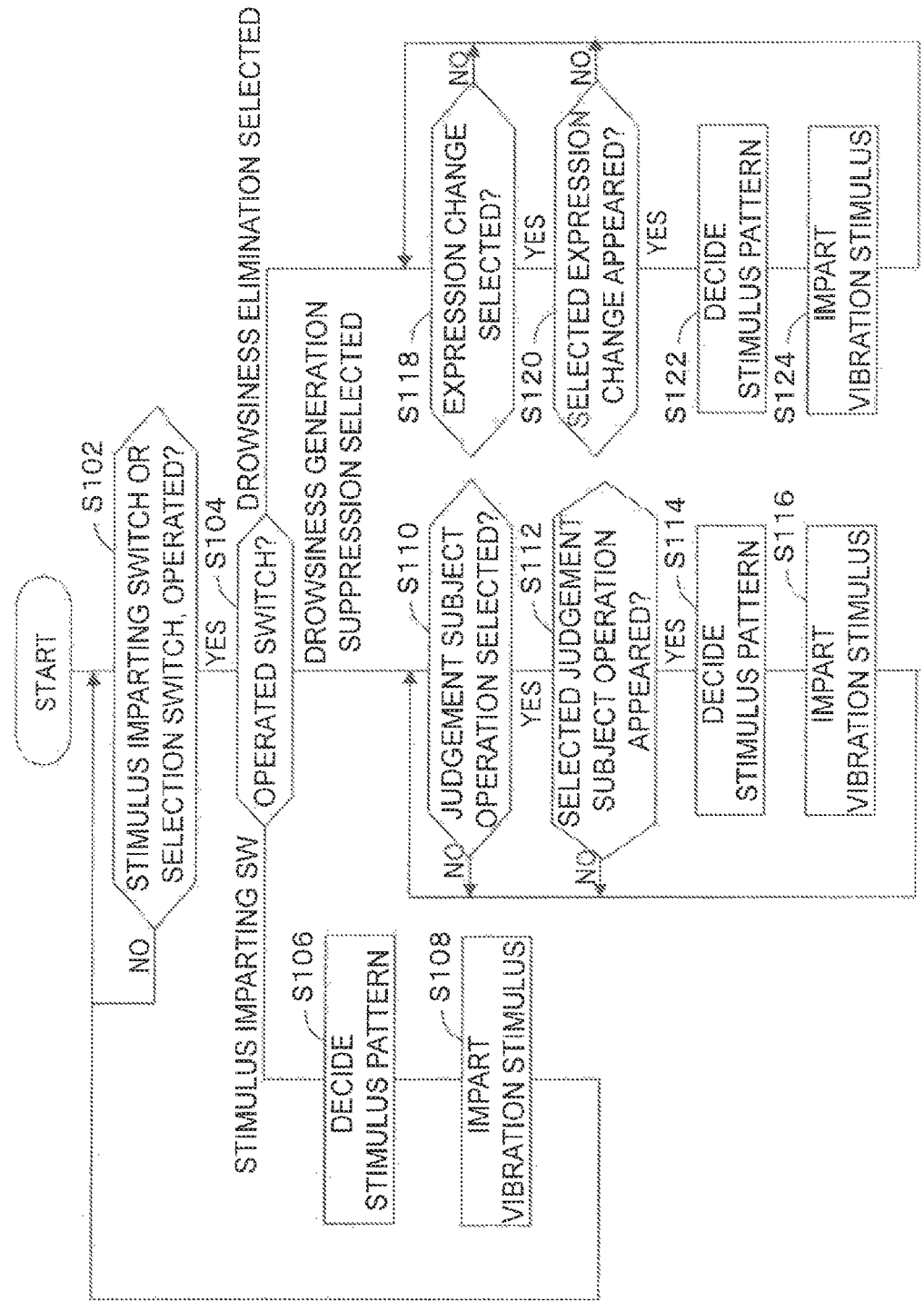
FIG. 13 is a flowchart of the control program to be executed by the control device shown in FIG. 1.
Figure 14:
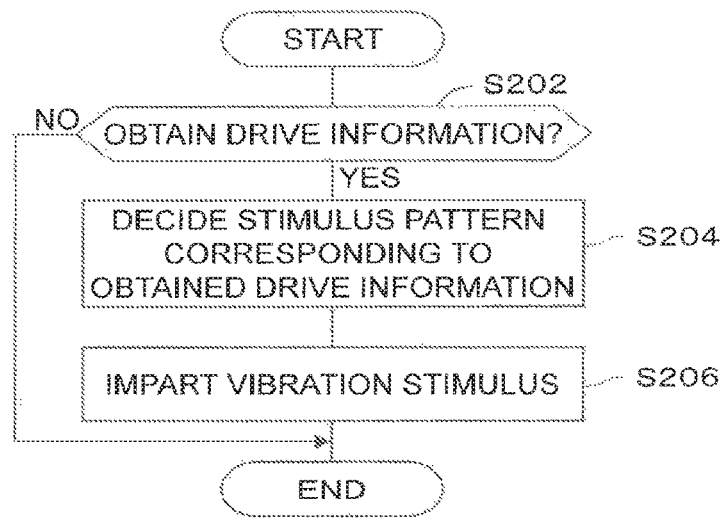
FIG. 14 is a flowchart of the control program to be executed by the control device shown in FIG. 1; and, FIG. 15 is an outline of the stimulus imparting device according to a second embodiment of the invention.

As explained, the operation of the stimulus imparting device 10 structured above will be explained hereinafter with the flowcharts shown in FIGS. 13 and 14. The control device 40, as similar to the above explained switch state obtaining/judging portion 41, obtains and judges each of the switch states of the selection switch 36 and the stimulus imparting switch 37 at the step S102. In other words, the control device 40 judges whether or not the selection switch 36 and the stimulus imparting switch 37 are operated.

When the selection switch 36 and the stimulus imparting switch 37 are not operated, the control device 40 repeatedly executes the process of the step S102. When the selection switch 36 and the stimulus imparting switch 37 are operated, the control device 40 advances the program to the step S104 and the steps thereafter.

At the step S104, the control device 40, as similar to the above explained switch state obtaining/judging portion 41, judges the states of the switches. The control device 40 advances the program to the step S106 when the stimulus imparting switch 37 is turned ON and advances the step S110 when the drowsiness generation suppression assist is selected by the selection switch 36. Further, the control device 40 advances the program to the step S118 when the drowsiness elimination assist is selected by the selection switch 36.

When the stimulus imparting switch 37 is turned ON (i.e., when the driver M itself requires the stimulus), the control device 40 decides the fourth stimulus pattern at the step S106, as similar to the above explained fourth stimulus pattern deciding portion 44*d* and the control device 40 drives vibration devices 12R, 12L, 13R and 13L to vibrate, based on the decided fourth stimulus pattern to impart the stimulus to the driver M to execute the drowsiness elimination assist for the driver M at the step S108, as similar to the above explained drive control portion 46.

At the steps S104, S110 and S112, the control device 40 judges whether or not the suppression of generation of the drowsiness of the driver M seating on the vehicle seat 20 (drowsiness generation suppression) is necessary (first judging portion), as similar to the above explained drowsiness generation suppression judging portion 42. In more detail, when the judgment subject operation is selected (decided) (at the step S110; YES) and when the selected judgement subject operation appears (at the step S112; YES), the control device 40 judges that the suppression of generation of the drowsiness of the driver M is necessary.

When the suppression of generation of the drowsiness of the driver M is judged to be necessary, the control device 40 decides the first stimulus pattern at the step S114, as similar to the above explained first stimulus pattern deciding portion 44*a* and then at the step S116, the control device 40 drives the vibration devices 12R, 12L, 13R and 13L to vibrate, based on the decided first stimulus pattern to impart the stimulus to the driver M to execute the drowsiness generation suppression assist for the driver M, as similar to the above explained drive control portion 46.

At the steps S104, S118 and S120, the control device 40 judges whether or not the elimination of the drowsiness of the driver M seating on the vehicle seat 20 (drowsiness elimination judgement) is necessary (second judging portion), as similar to the above explained drowsiness elimination judging portion 43. In more detail, when the judgment subject expression change is selected (decided) (At the step S118; YES) and when the selected judgement subject expression change appears (At the step S120; YES), the control device 40 judges that the elimination of the drowsiness of the driver M is necessary.

When the elimination of the drowsiness of the driver M is judged to be necessary, the control device 40 decides the second stimulus pattern at the step S122, as similar to the above explained second stimulus pattern deciding portion 44*b* and then at the step S124, the control device 40 drives the vibration devices 12R, 12L, 13R and 13L to vibrate, based on the decided second stimulus pattern to impart the stimulus to the driver M to execute the drowsiness elimination assist for the driver M, as similar to the above explained drive control portion 46.

The control device 40 obtains the drive information which relates to the drive of the vehicle A at the step S202, as similar to the drive information obtaining portion 45. When the control device 40 obtains the drive information, the control device 40 judges "YES" at the step S202 and advances the program to the step S204. When the control device 40 does not obtain the drive information, the control device 40 repeatedly judges "NO" at the step S202.

At the step S204, the control device 40 decides the third stimulus pattern, as similar to the third stimulus pattern deciding portion 44*c* and at the step S206, the control device 40 drives the vibration devices 12R, 12L, 13R and 13L to vibrate, based on the decided third stimulus pattern to impart the stimulus to the driver M to execute the drive information informing assist for the driver M, as similar to the above explained drive control portion 46.

As apparent from the first embodiment of the invention, the stimulus imparting device 10 according to the first embodiment includes at least one of a first vibration device 12 provided at the vehicle seat 20 (chair) on which the driver M (user) seats for imparting the stimulus to the tendon portion of musculus latissimus dorsi of the driver M and a second vibration device 13 provided at the vehicle seat 20 for imparting the stimulus to the tendon portion of musculus gluteus medius of the driver M and a control device 40 including a drive control portion 46 which imparts the stimulus to the driver M by drive-controlling at least one of the first vibration device 12 and the second vibration device 13.

According to the structure above, the drive control portion 46 imparts the stimulus to at least one of the tendon portion of musculus latissimus dorsi of the driver M by the first vibration device 12 and the tendon portion of musculus gluteus medius of the driver M by the second vibration device 13. In other words, the stimulus imparting device 10 can appropriately stimulate the portions which are highly effective in awakening the driver.

Further, the drowsiness generation suppression assist is greatly effective when the sleep debt of the subject is largely accumulated or the subject feels deeply fatigue. Further, since the drowsiness generation suppression assist and the drowsiness elimination assist can be selected by the request of the user, the negative mental state due to the stimulus can be reduced. Further, by selecting the judgement subject operation by the user, the user's consciousness to the subject operation can be raised and due to the vibration stimulus effect and the raised consciousness effect, the drowsiness generation suppression effect can be further raised.

Each stimulus imparted by the first and the second vibration devices 12 and 13 is set to be the frequency of 90 to 110 Hz and one time consecutive time for imparting is set to be 20 to 40 seconds. Accordingly, this stimulus imparting device 10 can impart the stimulus which is further appropriately effective to the portions where further awakening effect can be expected.

The control device 40 includes a drowsiness generation suppression judging portion 42 (first judging portion) which judges whether or not the suppression of generation of drowsiness of the driver M sitting on the vehicle seat 20 is necessary and a first stimulus pattern deciding portion 44a which decides the first stimulus pattern for suppressing the generation of the drowsiness when the generation of drowsiness of the driver M is judged to be necessary by the drowsiness generation suppression judging portion 42, wherein the drive control portion 46 imparts stimulus to the driver M by driving at least one of the first vibration device 12 and the second vibration device 13 to vibrate, based on the first stimulus pattern decided by the first stimulus pattern deciding portion 44a. According to the stimulus imparting device 10, the stimulus is properly imparted to the portions which are highly effective to the awakening effect and accordingly the generation of drowsiness can be sufficiently suppressed.

Further, the control device 40 includes a drowsiness elimination judging portion 43 (second judging portion) which judges whether or not the elimination of drowsiness of the driver M sitting on the vehicle seat 20 is necessary and a second stimulus pattern deciding portion 44b which decides the second stimulus pattern for eliminating the drowsiness when the elimination of drowsiness of the driver M is judged to be necessary by the drowsiness elimination judging portion 43, wherein the drive control portion 46 imparts stimulus to the driver M by driving at least one of the first vibration device 12 and the second vibration device 13 to vibrate, based on the second stimulus pattern decided by the second stimulus pattern deciding portion 44b. According to the stimulus imparting device 10, the stimulus is properly imparted to the portions which are highly effective to the awakening effect and accordingly the elimination of drowsiness can be sufficiently achieved.

Further, the chair is the vehicle seat 20 equipped in the vehicle A and the user is the driver of the vehicle A. According to this structure, the stimulus imparting device 10 which can properly impart the stimulus to the portions which are highly effective to the awakening effect can be applicable to the vehicle A. As a result, the drowsiness of the driver M of the vehicle A can be sufficiently suppressed or eliminated.

Further, in the stimulus imparting device 10, the chair corresponds to the vehicle seat 20 equipped in the vehicle A and the control device 40 further includes a drive information obtaining portion 45 which obtains the drive information relating to the drive information of the vehicle A and the third stimulus pattern deciding portion 44c which decides the third stimulus pattern in response to the types of the drive information relating to the drive of the vehicle A obtained by the drive information obtaining portion 45, wherein the drive control portion 46 imparts stimulus to the driver M seating on the vehicle seat 20 to execute the drive information informing assist operation by driving at least one of the first vibration device 12 and the second vibration device 13 to vibrate, based on the third stimulus pattern decided by the third stimulus pattern deciding portion 44c. According to the stimulus imparting device 10, the stimulus is properly imparted to the portions which are highly effective to the awakening effect, and accordingly the stimulus corresponding to the type of drive information can be appropriately given to the driver M and the drive information informing assist can be appropriately executed.

Further, the drive information relating to the drive of the vehicle A includes at least one of the guide information relating to the guide of the vehicle A and the vehicle surrounding information relating to the information surrounding the vehicle A. According to the drive information above, the driver M of the vehicle A receives stimulus in response to the guide information and the vehicle surrounding information for properly assisting the obtaining of the guide information and the vehicle surrounding information.

Second Embodiment

Figure 15:
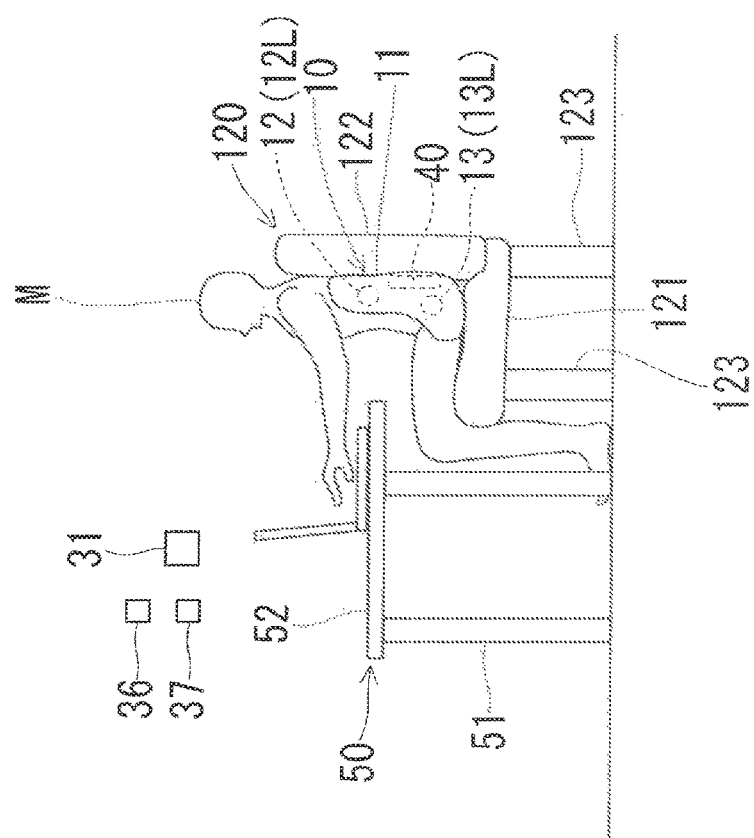

The second embodiment will be explained hereinafter with reference to FIG. 15. In the second embodiment, the present invention is different from the invention of the first embodiment (adoption to the vehicle A) in a point of adoption of the invention to the home appliance. In more detail, the vehicle seat 20 is changed to the chair 120, the acceleration sensor 34a, brake switch 35a, the surrounding information detecting sensor 32 and the car-navigation system 33 are not provided. The control device 40 is housed in the main body 11 of the stimulus imparting device 10.

The chair 120 is a chair in which the user seats and is formed by the seat cushion 121, the seat back 122 and a plurality of legs 123. The chair 120 is used with the desk 50 as a set. The desk 50 is formed by the base portion 52 and a plurality of legs 51. A user monitor 31, a selection switch 36 and a stimulus imparting switch 37 are arranged around the desk 50. Other structural elements are the same with those of the first embodiment and are referenced with the same numerals or symbols and the detail explanation thereof are omitted.

According to the structure of the second embodiment, as similar to the structure of the first embodiment, the stimulus imparting device 10 includes at least one of a first vibration device 12 provided at the chair 120 on which the user M seats, for imparting the stimulus to the tendon portion of musculus latissimus dorsi of the user M and a second vibration device 13 provided at the chair 120 for imparting the stimulus to the tendon portion of musculus gluteus medius of the user M and a control device 40 including a drive control portion 46 which imparts the stimulus to the user M by drive-controlling the at least one of the first vibration device 12 and the second vibration device 13.

According to the structure above, the drive control portion 46 imparts the stimulus to at least one of the tendon portion of musculus latissimus dorsi of the user M by the first vibration device 12 and the tendon portion of musculus gluteus medius of the user M by the second vibration device 13. In other words, the stimulus imparting device 10 can appropriately stimulate the portions which are highly effective in awakening the user.

It is noted that instead of using the stimulus imparting switch 37, a voice recognizing device can be provided for executing the stimulus requirement by voice.

The invention claimed is:

1. A stimulus imparting device comprising:
    at least one of a first vibration device provided at a chair to be positioned to face to a tendon portion of musculus latissimus dorsi of a user when the user is seated on the chair for imparting a stimulus to the tendon portion of musculus latissimus dorsi of the user and a second vibration device provided at the chair to be positioned to face to a tendon portion of musculus gluteus medius of the user when the user is seated on the chair for imparting the stimulus to the tendon portion of musculus gluteus medius of the user;
    a control device including a drive control portion which imparts the stimulus to the user by driving at least one of the first vibration device and the second vibration device;
    a first judging portion which judges whether or not a suppression of generation of drowsiness of the user sitting on the chair is necessary; and
    a first stimulus pattern deciding portion which decides a first stimulus pattern for suppressing the generation of the drowsiness when the generation of drowsiness of the user is judged to be necessary by the first judging portion, wherein
    the drive control portion imparts stimulus to the user by driving at least the one of the first vibration device and the second vibration device, based on the first stimulus pattern decided by the first stimulus pattern deciding portion.

2. The stimulus imparting device according to claim 1, wherein
    each stimulus imparted by the first vibration device and the second vibration device has a frequency of 90 to 110 Hz and a one-time consecutive imparting time is set to be 20 to 40 seconds.

3. The stimulus imparting device according to claim 1, further comprising:
    a second judging portion which judges whether or not an elimination of drowsiness of the user sitting on the chair is necessary; and
    a second stimulus pattern deciding portion which decides a second stimulus pattern for eliminating the drowsiness when the elimination of drowsiness of the user is judged to be necessary by the second judging portion, wherein
    the drive control portion imparts stimulus to the user by driving at least the one of the first vibration device and the second vibration device based on the second stimulus pattern decided by the second stimulus pattern deciding portion.

4. The stimulus imparting device according to claim 1, wherein
    the chair corresponds to a vehicle seat equipped in a vehicle and the user corresponds to a driver of the vehicle.

5. The stimulus imparting device according to claim 1, wherein
    the chair corresponds to a vehicle seat equipped in a vehicle,
    the control device further includes a drive information obtaining portion which obtains a drive information which is an information relating to a drive of the vehicle and a third stimulus pattern deciding portion which decides a third stimulus pattern in response to types of the drive information which is the information relating to the drive of the vehicle obtained by the drive information obtaining portion, and
    the drive control portion imparts stimulus to a driver seating on the vehicle seat by driving at least the one of the first vibration device and the second vibration device, based on the third stimulus pattern decided by the third stimulus pattern deciding portion.

6. The stimulus imparting device according to claim 5, wherein
    the drive information which is the information relating to the drive of the vehicle includes at least one of a guide information relating to a guide of the vehicle and a vehicle surrounding information which is the information on a surrounding of the vehicle.

* * * * *